United States Patent [19]

Blower et al.

[11] Patent Number: 5,682,875

[45] Date of Patent: Nov. 4, 1997

[54] AEROSOL DEVICE HAVING A SPOUT TO PREVENT SPRAY HEAD BLOCKAGE

[75] Inventors: Andrew William Blower, Ashby de la Zouch; Michael John Clarke, Shepshed; John Stuart Corbett, Loughborough, all of England

[73] Assignee: Fisons plc, Ipswich, England

[21] Appl. No.: 607,018

[22] Filed: Feb. 26, 1996

Related U.S. Application Data

[63] Continuation of Ser. No. 313,441, Sep. 27, 1994, abandoned, which is a continuation of Ser. No. 14,095, Feb. 4, 1993, abandoned, which is a continuation of Ser. No. 727,320, Jul. 2, 1991, abandoned, which is a continuation of Ser. No. 422,986, Oct. 16, 1989, abandoned.

[30] Foreign Application Priority Data

Oct. 22, 1988 [GB] United Kingdom ............ 88 24804

[51] Int. Cl.⁶ .................. A61M 11/00; A61M 15/00; A61M 16/10; B05B 7/32
[52] U.S. Cl. .................. 128/200.23; 128/200.14; 128/203.12; 239/337
[58] Field of Search .............. 128/200.14, 200.23, 128/203.12, 203.15, 200.18; 239/337

[56] References Cited

U.S. PATENT DOCUMENTS

| 1,378,481 | 5/1921 | Mobley | 128/200.23 |
|---|---|---|---|
| 3,001,524 | 9/1961 | Maison et al. | 128/200.23 |
| 3,006,340 | 10/1961 | Meshberg | 128/200.23 |
| 3,116,856 | 1/1964 | Prussin et al. | 128/200.23 |
| 3,154,076 | 10/1964 | O'Donnell | 128/200.23 |
| 3,302,834 | 2/1967 | Alsop | 128/200.23 |
| 3,913,842 | 10/1975 | Singer | 239/337 |
| 4,811,731 | 3/1989 | Newell et al. | 128/203.15 |

FOREIGN PATENT DOCUMENTS

| 728952 | 3/1966 | Canada | 128/200.23 |
|---|---|---|---|
| 0089070 | 9/1983 | European Pat. Off. | 128/200.23 |
| 0132352 | 1/1985 | European Pat. Off. | 128/200.23 |
| 105263 | 1/1897 | Germany | 128/200.23 |
| 99363 | 9/1897 | Germany | 128/200.23 |
| 2218394 | 10/1973 | Germany | 128/200.23 |
| 763570 | 12/1956 | United Kingdom | 128/200.23 |
| 2196262 | 4/1988 | United Kingdom | 128/200.23 |
| 8502347 | 6/1985 | WIPO | 128/200.14 |

OTHER PUBLICATIONS

European Search Report, Ap. #EP 89 31 0314, The Hague, 24-01-1990 (2 sheets).
"The Fluid Mechanics of Cromolyn Sodium Inhalers ..." Proceedings from 7th New (NE) Bio. Conf., Tray, N.Y., Niemi et al, 1979.

*Primary Examiner*—Kimberly L. Asher
*Attorney, Agent, or Firm*—Marshall, O'Toole, Gerstein, Murray & Borun

[57] ABSTRACT

An aerosol inhalation device suitable for use in association with a pressurized medicament container having a valve stem has a spray head adapted to receive the valve stem. The spray head has an outlet orifice of uniform diameter which is provided with a spout to prevent blockage of the spray head. The device is especially useful in the administration of hygroscopic medicaments, for example sodium cromoglycate or nedocromil sodium.

8 Claims, 1 Drawing Sheet

AEROSOL DEVICE HAVING A SPOUT TO PREVENT SPRAY HEAD BLOCKAGE

CROSS-REFERENCE TO RELATED APPLICATION

This is a continuation of U.S. application Ser. No. 08/313,441, filed Sep. 27, 1994, now abandoned; which is a continuation of Ser. No. 08/014,095 filed Feb. 4, 1993, now abandoned; which is a continuation of Ser. No. 07/727,320 filed Jul. 2, 1991, now abandoned; which is a continuation of Ser. No. 07/422,986 filed Oct. 16, 1989, now abandoned.

This invention relates to improvements in aerosol devices, more particularly to those for the dispensing of medicaments for inhalation.

BACKGROUND OF THE DISCLOSURE

The use of aerosol inhalation devices for the administration by inhalation of medicaments in the form of powder aerosols is well known. Such devices generally comprise a housing which receives a canister of pressurised medicament. The canister is provided with a dispensing metering valve including a metering chamber and a hollow valve stem which locates in a spray head within the housing.

Medicament is discharged by moving the canister relative to the valve stem. This changes the dispensing metering valve from an inoperative state in which the metering chamber is isolated from the atmosphere to an operative state in which the metering chamber communicates with the atmosphere via the valve stem and an outlet orifice provided in the spray head. Thus, in the operative state medicament can pass from the chamber through the valve stem, the spray head and the outlet orifice into the housing from where it can be inhaled by a user via a mouthpiece formed in the housing.

A problem which can occur with devices of this type is blockage of the outlet orifice. Also, medicament may build up around the outlet orifice and form a plug which may subsequently be dislodged and inhaled by the user.

We have now surprisingly found that these problems can be eliminated or substantially mitigated by providing the outlet orifice with a spout.

Thus, according to the present invention there is provided an aerosol inhalation device suitable for use in association with a pressurised medicament container having a valve stem, the device comprising a spray head adapted to receive the valve stem and having an outlet orifice, characterised in that the outlet orifice is provided with a spout.

We prefer the spout to be generally frusto-conical in shape. We particularly prefer the spout to be frusto-conical and the curved outer surface of such a spout to be concave.

We prefer the spout to be less than 10 mm and more preferably less than 5 mm in length, for example 2 mm. The ratio of the length of the outlet orifice to the length of the spout is preferably less than 2:1.

The spray head includes an internal cavity which is open at one end to receive the valve stem and closed at the other end. The cavity may extend beyond the outlet orifice.

We prefer the outlet orifice to be of uniform cross section throughout its length. We further prefer the outlet orifice to be circular in cross section.

The device of the present invention is used in conjunction with a canister of pressurised medicament. Thus, the present invention further provides an aerosol inhalation device comprising a pressurised medicament container having a valve stem, a spray head adapted to receive the valve stem and having an outlet orifice, characterised in that the outlet orifice is provided with a spout.

We have found that the problem of blockage is particularly marked when the medicament is hygroscopic. Thus, the spouted inhalation devices of the present invention are particularly useful for administering hygroscopic medicaments.

By "hygroscopic medicament" we mean a medicament which takes up significant amounts of water when in a moist atmosphere, for example one which at 90% relative humidity (being approximately a lower value for the relative humidity found in human breath) takes up more than 8% of its own weight of water. Examples of such medicaments include sodium cromoglycate and nedocromil sodium.

The aerosol inhalation devices of the invention have the advantages that they do not become blocked or block less frequently, so that a canister of medicament can be exhausted without the danger of the device being discarded prematurely because the patient mistakenly believes that the canister is empty or because it cannot readily be unblocked; there is a greatly reduced risk of plugs of medicament forming in the devices which are subsequently inhaled by the patient—such inhalation may lead to over-dosing or a coughing spasm which is especially dangerous for patients who have breathing difficulties and who are most likely to be using aerosol inhalation devices; the devices are more hygienic because there are fewer or no medicament accretion surfaces which bacteria may colonize; and they need to be cleaned less frequently—cleaning being a difficult task for patients who have unsteady hands.

BRIEF DESCRIPTION OF THE FIGURES

A preferred embodiment of a device according to the invention will now be described, by way of example, with reference to the accompanying drawings, in which.

DETAILED DESCRIPTION

Figure 1:
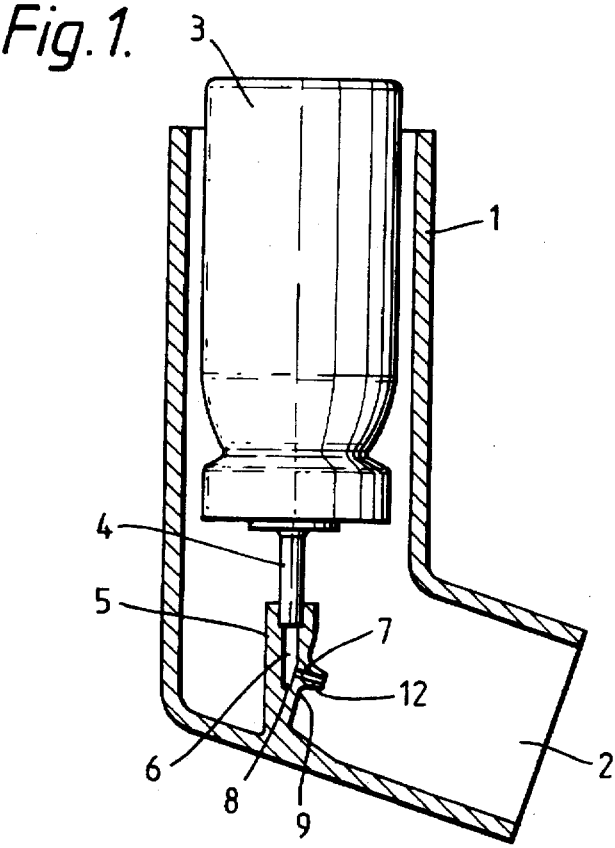
FIG. 1 is a side view in partial section of an aerosol inhalation device according to the invention fitted with a pressurised medicament container.

Referring first to FIG. 1, an aerosol inhalation device comprises a generally cylindrical housing 1 having a mouthpiece 2. The housing 1 receives a container 3 of pressurised medicament, the container being provided at one end with a metering valve including a valve stem 4. The valve stem 4 is seated in a spray head 5. The spray head 5 includes an internal cavity 6 provided with an outlet orifice 7. The internal cavity 6 has a lower portion 8 which extends below the outlet orifice 7.

Figure 2:
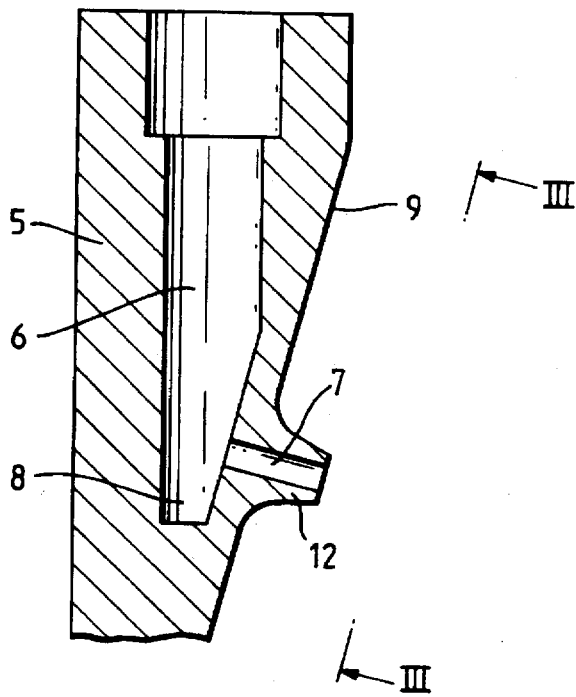
FIG. 2 is an expanded view of the spray-head of the device shown in FIG. 1 (also here in cross-section)
Figure 3:
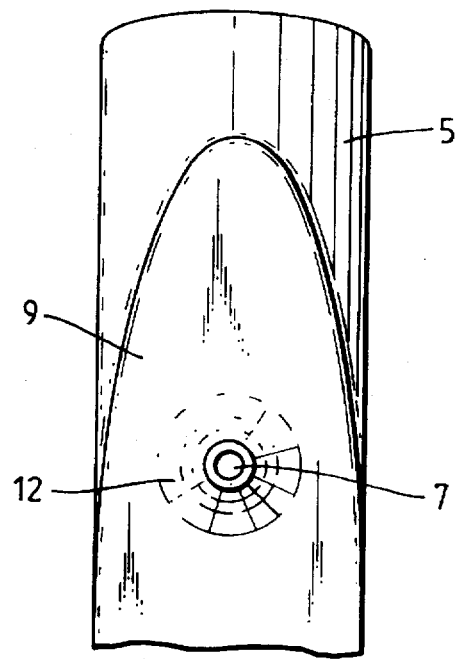
FIG. 3 is a view of the spray-head shown in FIG. 2 along the line III—III.

As can be seen more clearly from FIG. 2, the outlet orifice 7 passes through a spout 12 which has a generally frusto-conical shape with a concave outer wall. The spout 12 rises out of a flat front surface 9 of the spray head 5, the flat surface being at an angle such that the spout 12 is directed towards the mouthpiece 2.

To use the device, a patient inhales at the mouthpiece 2 while simultaneously urging the medicament container 3 towards the spray head 5. The relative motion of the container 3 and the valve stem 4 causes the metering valve to open and medicament to be discharged into the valve stem 4. The medicament then passes through the internal cavity 6 of the spay head, and finally through the outlet orifice 7 after which it is inhaled by the patient through the mouthpiece 2.

We claim:

1. An aerosol inhalation device comprising a housing having a mouthpiece, a pressurized container of medicament having a valve stem received in said housing, a spray head mounted in said housing having an outlet orifice and adapted to receive the valve stem, the device further comprising means for minimizing blockage of said outlet orifice comprising a frustoconical spout rising out of the spray head, said spout being less than 5 mm in length, said outlet orifice extending through said spout and having a uniform cross section throughout its length.

2. The device as claimed in claim 1 wherein the medicament is hygroscopic.

3. The device as claimed in claim 2 wherein said hygroscopic medicament is sodium cromoglycate or nedocromil sodium.

4. The device as claimed in claim 1 wherein said spout is less than 2 mm in length.

5. The device as claimed in claim 1 wherein said spout has a concave outer surface.

6. The device as claimed in claim 1 wherein the ratio of the length of the outlet orifice to the length of the spout is less than 2:1.

7. The device as claimed in claim 1 wherein the outlet orifice is circular in cross section.

8. The device as claimed in claim 1 wherein the spray head includes an internal cavity which is open at one end to receive the valve stem and closed at the other end, the cavity extending beyond the outlet orifice.

* * * * *